(12) United States Patent
Barnett

(10) Patent No.: US 9,345,257 B2
(45) Date of Patent: *May 24, 2016

(54) METHOD AND PRODUCTS FOR ENHANCING DRUG AND DIETARY SUPPLEMENT BIOAVAILABILITY

(71) Applicant: CBA Pharma, Inc., Lexington, KY (US)

(72) Inventor: Daryl L. Barnett, Lexington, KY (US)

(73) Assignee: CBA Pharma, Inc., Lexington, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/206,633

(22) Filed: Mar. 12, 2014

(65) Prior Publication Data

US 2014/0275140 A1    Sep. 18, 2014

Related U.S. Application Data

(60) Provisional application No. 61/792,700, filed on Mar. 15, 2013.

(51) Int. Cl.
| | |
|---|---|
| *A61K 31/4725* | (2006.01) |
| *A61K 45/06* | (2006.01) |
| *A23L 1/30* | (2006.01) |
| *A61K 31/4741* | (2006.01) |

(52) U.S. Cl.
CPC .............. *A23L 1/30* (2013.01); *A61K 31/4741* (2013.01); *A61K 45/06* (2013.01)

(58) Field of Classification Search
CPC ....... A61K 31/4725; A61K 45/06; A23L 1/30
USPC ........................................................ 514/308
See application file for complete search history.

(56) References Cited

U.S. PATENT DOCUMENTS

| | | | |
|---|---|---|---|
| 6,086,915 A | 7/2000 | Zeligs et al. | |
| 6,911,454 B1 | 6/2005 | Van Dyke | |
| 2007/0027181 A1 | 2/2007 | Nakajima | |
| 2014/0275140 A1 | 9/2014 | Barnett | |
| 2014/0275157 A1* | 9/2014 | Barnett | A61K 45/06 514/308 |

OTHER PUBLICATIONS

Li, et al., Paclitaxel/Tetrandrine Coloaded Nanoparticles Effectively Promote the Apoptosis of Gastric Cancer Cells Based on "Oxidation Therapy", Mol. Pharmaceutics, 9, 222-229 (2012).*
Li et al., Paclitaxel/Tetrandrine Coloaded Nanoparticles Effectively Promote the Apoptosis of Gastric Cancer Cells Based on "Oxidation Therapy," American Chemical Society 2011, pp. 222-229.

* cited by examiner

*Primary Examiner* — Erich A Leeser
(74) *Attorney, Agent, or Firm* — Mitchell Intellectual Property Law, PLLC

(57) ABSTRACT

Enhancing the bioavailability of a drug or dietary supplement by administering it concurrently with one or more members of the d-tetrandrine family.

20 Claims, No Drawings

METHOD AND PRODUCTS FOR ENHANCING DRUG AND DIETARY SUPPLEMENT BIOAVAILABILITY

CROSS REFERENCE TO RELATED APPLICATIONS

The present application claims the benefit of U.S. Provisional Patent Application No. 61/792,700, entitled METHOD AND PRODUCTS FOR ENHANCING DRUG AND DIETARY SUPPLEMENT BIOAVAILABILITY, filed on Mar. 15, 2013, the entire contents of which are incorporated by reference.

FIELD AND BACKGROUND OF THE INVENTION

The present invention relates to the oral administration of drugs and dietary supplements, including nutraceuticals. The effectiveness of drugs and dietary supplements is in part a function of their bioavailability following oral ingestion or anal adsorption. Generally, the term bioavailability is the fraction of, and rate at which, an administered dose of unchanged drug is adsorbed through the lining of the alimentary canal into systemic circulation. Bioavailability for dietary supplements is similar, and is generally defined as the proportion of the administered substance capable of being absorbed and available for use or storage. In both pharmacology and nutrition sciences, bioavailability is measured by calculating the area under the curve (AUC) of the drug or dietary supplement concentration time profile.

SUMMARY OF THE INVENTION

In the present invention, bioavailability of drugs and dietary supplements is enhanced by the concurrent administration of particular members of the d-tetrandrine family of drugs. The d-tetrandrine family members have the following structural formula:

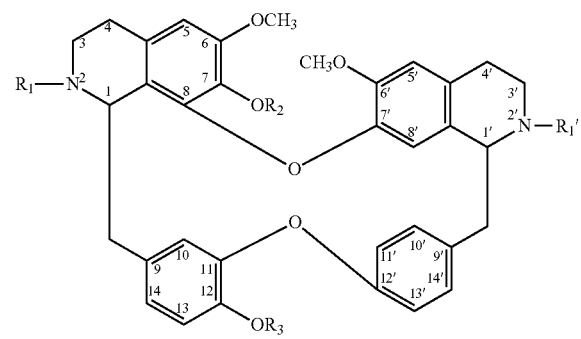

Where $R_1$ and $R_1'$ are the same or different shortchained carbon based ligand including without limitation. $CH_3$, $CO_2CH_3$ or H; and $R_2$ is $CH_3$ or $C_2H_5$; and $R_3$ is $CH_3$ or hydrogen; and where the chemical structure has the "S" isomeric configuration at the C-1' chiral carbon location.

DESCRIPTION OF THE PREFERRED EMBODIMENT

The preferred members of the d-tetrandrine family include the following representative examples, which are not intended to be exhaustive: d-tetrandrine, isotetrandrine, hernandezine, berbamine, pycnamine, phaeanthine, obamegine, ethyl fangchinoline and fangchinoline. In all of these examples, $R_1$ and $R_1'$ constitute the methyl group. Variation within the group occurs in that $R_2$ and $R_3$ may constitute either a methyl group or hydrogen, and the isometric configuration of the compounds at the C-1 and C-1' chiral carbon positions is either R (rectus) or S (sinister). The rules for R and S configuration can be found in Morrison and Boyd, "Organic Chemistry," $4^{th}$ Edition, copyright 1983 by Allyn and Bacon, at pp. 138-141. As noted above, the chiral configuration at C-1' is "S" for members of the d-tetrandrine family. In addition, hernandezine includes a methoxy group at the C-5 position.

The most preferred member of the claimed tetrandrine family is d-tetrandrine. Methods for extracting and/or purifying d-tetrandrine are disclosed in U.S. Pat. No. 6,218,541 and in Published Patent Application No. 2011/0105755.

Drugs and dietary supplements are adsorbed through the lining of the alimentary canal at different rates. The extent to which concurrent administration of a d-tetrandrine family member enhances the extend and rate of such adsorption will also vary accordingly. Those drugs and dietary supplements with rapid and more complete rates of adsorption may show little or no improvement in bioadsorption and bioavailability through the concurrent use of a d-tetrandrine family member. However, many drugs and dietary supplements with slower and less complete rates of bioadsorption and bioavailability will show improved bioavailability with such concurrent use.

The d-tetrandrine family member and the drug or dietary supplement can be formulated together into a single formula, they can be formulated separately and administered either simultaneously or sufficiently close together that they are both in the alimentary canal at the same time, or they can be administered such that the d-tetrandrine family member is available in the lining of the alimentary canal at the time the drug or dietary supplement is ingested. The d-tetrandrine family member and the drug or dietary supplement can be formulated separately but be sold as part of a "kit." The usage ratio of the d-tetrandrine family member to a drug or dietary supplement will vary from patient to patient and as a function of the principle drug or dietary supplement used, within a range of from about 0.04:1 to about 170:1. A more typical range would be from about 1:1 to 100:1, more preferably from 25:75 to 75:25.

It is believed that the optimum dosage procedure would be to administer the d-tetrandrine family member in oral doses of from about 50 to about 1000 mg per square meter per day, more preferably 250-700, and most preferably about 500, (probably in two to four doses per day), while administering the drug or dietary supplement simultaneously or on the same day. The dosage level for the d-tetrandrine family member will vary from case to case, based on the patient and on the drug or dietary supplement used. The drug or dietary supplement is administered at usual dosage levels (possibly somewhat less in view of the effect of the d-tetrandrine member on bioavailability) once or more during the course of the d-tetrandrine family member dosing.

The d-tetrandrine family bisbenzylisoquinolines have two nitrogen locations and hence can exist in the free base form or as a mono or di-acid salt. Because of the enhanced solubility of the salt form of pharmaceutical ingredients, the salt forms are used in formulating pharmaceutical compositions. The active ingredient thus solubilizes more quickly and enters the bloodstream faster. The free base form is not soluble in water. However, it has recently been surprisingly found by a co-worker that the free base formulations of d-tetrandrine family members are absorbed into the bloodstream substantially as rapidly as formulations of the di-acid salt members of the family. Accordingly, we propose to use either the free base or the di-acid salt of the d-tetrandrine family member in our formulations.

The preferred formulations comprise a member of the d-tetrandrine family combined with a suitable pharmaceutical carrier. The pharmaceutical carrier can be a liquid of a solid composition. A liquid carrier will preferably comprise water, possibly with additional ingredients such as 0.25% carboxymethlcellulose. The solid carrier or diluent used may be pregelatinized starch, microcrystalline cellulose or the like. It may also be formulated with other ingredients, such as colloidal silicone dioxide, sodium lauryl sulfate and magnesium stearate.

A 200 mg capsule, tablet or liquid dosage formulation is most preferred. The most preferred dose of about 500 mg/square meter/day is roughly 1000 mg per day for a 190 pound patient six feet tall. Such a patient can fulfill the dosage requirements by taking five capsules during the course of the day, for example three in the morning and two in the evening, or one at a time spaced out over the day. A smaller person weighing 125 pounds at a height of five feet six inches would require four 200 mg capsules during the course of the day.

Of course, it is understood that the forgoing are preferred embodiments of the invention, and that variations can be employed without departing from the spirit of the invention as set forth in the appended claims, interpreted in accordance with the principles of patent law.

The invention claimed is:

1. A method of enhancing the bioavailability of drugs and dietary supplements which show slow and/or incomplete bioadsorption and bioavailability comprising: the concurrent administration of a drug or dietary supplement and a member of the d-tetrandrine family of drugs having the following structural formula:

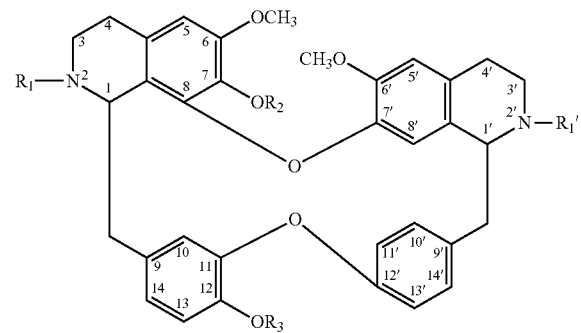

where $R_1$ and $R_1'$ are the same or different short chained carbon based ligand including without limitation, $CH_3$, $CO_2CH_3$ or H; and $R_2$ is $CH_3$ or $C_2H_5$; and $R_3$ is $CH_3$ or hydrogen, and wherein said structural formula has the "S" isomeric configuration at the C-1' chiral carbon location, said concurrent administration being such that said d-tetrandrine family member and said drug or dietary supplement are present in the alimentary canal at the same time, or such that said d-tetrandrine member is available in the lining of the alimentary canal when the drug or dietary supplement is ingested.

2. The method of claim 1 wherein said member of the d-tetrandrine family is selected from the group consisting of: d-tetrandrine, isotetrandrine, hernandezine, berbamine, pycnamine, phaeanthine, obamegine, ethyl fangchinoline and fangchinoline.

3. The method Of claim 1 wherein said member of the d-tetrandrine family is d-tetrandrine.

4. The method of claim 3 in which the d-tetrandrine family member is used in conjunction with a drug.

5. The method of claim 4 in which the d-tetrandrine family member and the drug are formulated together into a single formula.

6. The method of claim 1 in which the d-tetrandrine family member is used in conjunction with a drug.

7. The method of claim 1 in which the drug or dietary supplement normally has a rate of bioavailability which is at the slower and/or less complete one third portion of on a scale of bioavailability for various drugs and dietary supplement.

8. The method of claim 1 in which the d-tetrandrine family member and the drug or dietary supplement are formulated together into a single formula.

9. The method of claim 1 in which the d-tetrandrine family member and the drug or dietary supplement are formulated separately and administered either simultaneously or sufficiently close together that the MRSA is exposed to both simultaneously.

10. The method of claim 1 in which the d-tetrandrine family member and drug or dietary supplement are administered in a usage ratio of d-tetrandrine family member to drug or supplement, within a range of from about 0.04 to about 170.

11. The method of claim 1 in which the d-tetrandrine family member and drug or dietary supplement are administered in a usage ratio of d-tetrandrine family member to drug or dietary supplement, within a range of from about 1 to 100.

12. The method of claim 1 in which the d-tetrandrine family member and drug or dietary supplement are administered in a usage ratio of d-tetrandrine family member to drug or dietary supplement, within a range of from about 25:75 to 75:25.

13. A method of enhancing the bioavailability of dietary supplements which show slow and/or incomplete bioadsorption and bioavailability comprising:

the concurrent administration of a dietary supplement and a member of the d-tetrandrine family of drugs having the following structural formula:

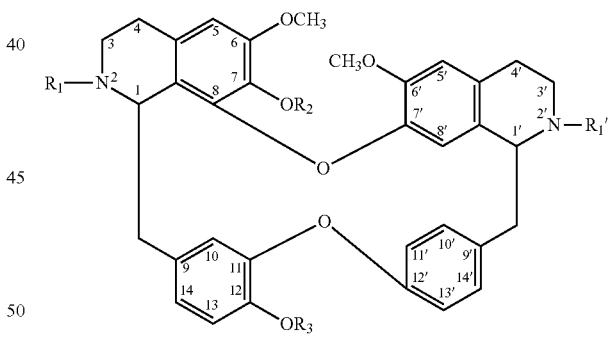

where $R_1$ and $R_1'$ are the same or different short chained carbon based ligand including without limitations, $CH_3$, $CO_2CH_3$ or H; and $R_2$ is $CH_3$ or $C_2H_5$; and $R_3$ is $CH_3$ or hydrogen, and wherein said structural formula has the "S" isomeric configuration at the C-1' chiral carbon location, said concurrent administration being such that said d-tetrandrine family member and said drug or dietary supplement are resent in the alimentary canal at the same time or such that said d-tetrandrine member is available in the lining of the alimentary canal when the drug or dietary supplement is ingested.

14. The method of claim 13 wherein said member of the d-tetrandrine family is d-tetrandrine.

15. The method of claim 14 in which the d-tetrandrine family member and the dietary supplement are formulated together into a single formula.

16. A method of enhancing the bioavailability of drugs and dietary supplements which show slow and/or incomplete bioadsorption and bioavailability comprising: the concurrent administration of a drug or dietary supplement and a member of the d-tetrandrine family of drugs having the following structural formula:

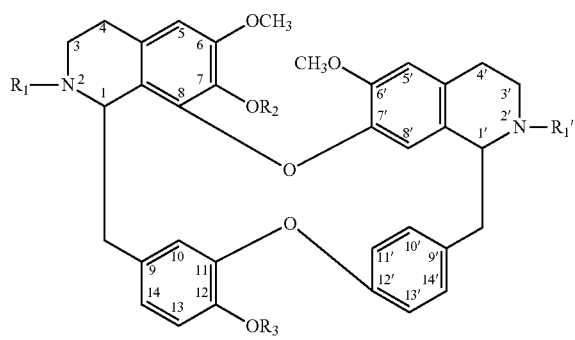

where $R_1$ and $R_1'$ are the same or different short chained carbon based ligand including without limitation $CH_3$, $CO_2CH_3$ or H; and $R_2$ is $CH_3$ or $C_2H_5$; and $R_3$ is $CH_3$ or hydrogen, and wherein said structural formula has the "S" isomeric configuration at the C-1' chiral carbon location, said concurrent administration being such that said d-tetrandrine family member and said drug or dietary supplement are present in the alimentary canal at the same time, or such that said d-tetrandrine member is available in the lining of the alimentary canal when the drug or dietary Supplement is ingested, said d-tetrandrine family member being administered, in oral doses of from about 50 to about 1000 mg per square meter per day over a period of from about 4 to about 14 days, and the drug or dietary supplement is then administered at usual dosage levels once or more during said 4 to 14 days.

17. A method of enhancing the bioavailability of drugs and dietary supplements which show slow and/or incomplete bioadsorption and bioavailability comprising: the administration of a formulation of a drug or dietary supplement and a member of the d-tetrandrine family of drugs having the following structural formula:

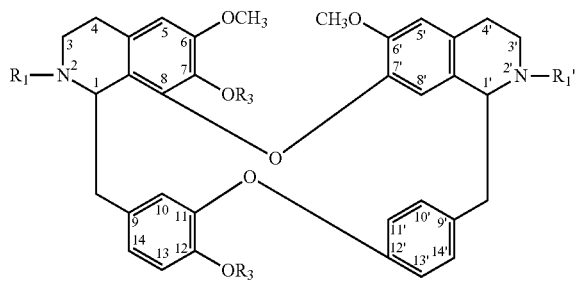

where $R_1$ and $R_1'$ are the same or different short chained carbon based ligand including without limitation $CH_3$, $CO_2CH_3$ or H; and $R_2$ is $CH_3$ or $C_2H_5$; and $R_3$ is $CH_3$ or hydrogen, and wherein said structural formula has the "S" isomeric configuration at the C-1' chiral carbon location, said formulation being administered, such that said d-tetrandrine family member is administered in oral doses of from about 250-700 mg per square meter per day over said period of from about 4 to about 14 days.

18. A method of enhancing the bioavailability of drugs and dietary supplements which show slow and/or incomplete bioadsorption and bioavailability comprising: the administration of a formulation of a drug, or dietary supplement and a member of the d-tetrandrine family of drugs hay inn the following structural formula:

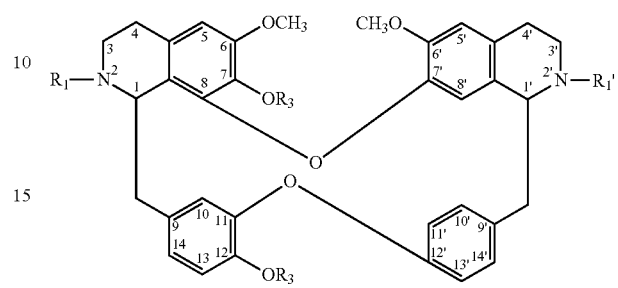

where $R_1$ and $R_1'$ are the same or different short chained carbon based ligand including without limitation $CH_3$, $CO_2CH_3$ or H; and $R_2$ is $CH_3$ or $C_2H_5$; and $R_3$ is $CH_3$ or hydrogen, and wherein said structural formula has the "S" isomeric configuration at the C-1' chiral carbon location, said formulation being administered such that said d-tetrandrine family member is administered in oral doses of about 500 mg per square meter per day over said period of from about 4 to about 14 days, in two to four doses per day.

19. A dietary supplement composition comprising, a dietary supplement combined with a member of the d-tetrandrine family having the following structural formula:

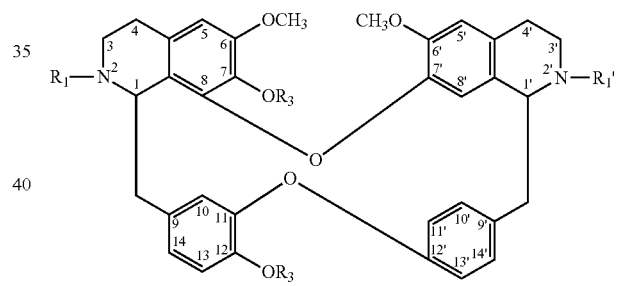

where $R_1$ and $R_1'$ are the same or different short chained carbon based ligand including without limitation, $CH_3$, $CO_2CH_3$ or H; $R_2$ is $CH_3$ or $C_2H_5$; and $R_3$ is $CH_3$ or hydrogen, and wherein said structural formula has the "S" isomeric configuration at the C-1' chiral carbon location.

20. A kit including a dietary supplement, and a formulation comprising a member of the d-tetrandrine family having the following structural formula:

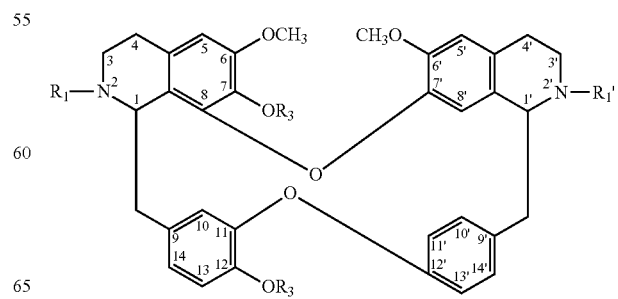

where $R_1$ and $R_1'$ are the same or different short chained carbon based ligand including without limitation, $CH_3$, $CO_2CH_3$ or H; and $R_2$ is $CH_3$ or $C_2H_5$; and $R_3$ is $CH_3$ or hydrogen, and wherein said structural formula has the "S" isomeric configuration at the C-1' chiral carbon location.

* * * * *